United States Patent [19]

Clark, Jr.

[11] Patent Number: 5,030,333

[45] Date of Patent: Jul. 9, 1991

[54] POLAROGRAPHIC METHOD FOR MEASURING BOTH ANALYTE AND OXYGEN WITH THE SAME DETECTING ELECTRODE OF AN ELECTROENZYMATIC SENSOR

[75] Inventor: Leland Clark, Jr., Cincinnati, Ohio

[73] Assignee: Children's Hospital Medical Center, Cincinnati, Ohio

[21] Appl. No.: 918,628

[22] Filed: Oct. 14, 1986

Related U.S. Application Data

[63] Continuation of Ser. No. 650,344, Sep. 13, 1984, abandoned.

[51] Int. Cl.$^5$ .............................................. G01N 27/48
[52] U.S. Cl. ............................ 204/153.1; 204/153.12; 204/153.16; 128/635
[58] Field of Search ............... 204/1 T, 1 Y, 1 P, 1 E, 204/403, 415, 418, 153.1, 153.12, 153.16, 153.17; 435/817; 128/637, 639, 642, 635

[56] References Cited

U.S. PATENT DOCUMENTS

| | | | |
|---|---|---|---|
| 3,380,905 | 4/1968 | Clark, Jr. ......................... 204/415 |
| 3,539,455 | 11/1970 | Clark, Jr. ......................... 204/1 E |
| 3,542,662 | 11/1970 | Hicks et al. ...................... 204/1 E |
| 4,281,659 | 8/1981 | Farrar et al. ..................... 128/635 |
| 4,340,458 | 7/1982 | Lerner et al. ................. 128/635 X |
| 4,356,074 | 10/1982 | Johnson ........................ 204/1 E X |
| 4,401,122 | 8/1983 | Clark, Jr. ......................... 128/635 |
| 4,431,004 | 2/1984 | Bessman et al. .............. 204/403 X |
| 4,452,682 | 6/1984 | Takata et al. ................ 204/415 X |
| 4,458,686 | 7/1984 | Clark, Jr. ......................... 128/635 |
| 4,467,811 | 8/1984 | Clark, Sr. ....................... 204/403 X |

FOREIGN PATENT DOCUMENTS 0041191  4/1979  Japan .................................. 435/817

*Primary Examiner*—Nam X. Nguyen
*Attorney, Agent, or Firm*—Wood, Herron & Evans

[57] ABSTRACT

Novel polarographic (voltametric) methods for measuring in vivo or in vitro analytes in an animal tissue and oxygen in the sensor enzymatic reaction layer with an electroenzymatic sensor are disclosed. The new and vastly improved methods are directed to generating from the electroenzymatic sensor at a suitable voltage an anodic current derived from an anodically active product generated by enzymatic activity on an analyte for measuring the analyte and a cathodic current derived from reducing the oxygen in the sensor enzymatic reaction layer for measuring the oxygen. Additionally, the method contemplates switching the voltage between anodic and cathodic potentials to generate anodic and cathodic currents or applying the voltage at a fixed rate. Advantageously, the methods of this invention may be utilized with implanted sensors in an animal including a human. The sensors may be implanted in blood or non-blood sites. Finally, the methods of this invention further contemplate analyzing the type of conditions around the implanted sensor site to improve the reliability of the sensor as well as the detection of the analyte by the sensor.

11 Claims, No Drawings

POLAROGRAPHIC METHOD FOR MEASURING BOTH ANALYTE AND OXYGEN WITH THE SAME DETECTING ELECTRODE OF AN ELECTROENZYMATIC SENSOR

This application is a continuation, of application Ser. No. 650,344, filed Sep. 13, 1984.

BACKGROUND OF THE DISCLOSURE

Electrochemical sensors for blood analysis in clinics, intensive care units and surgical units are well known in the art. Such sensors have been utilized for measuring various materials qualitatively and quantitatively to enhance the metabolic surveillance of patients. For instance, electrochemical sensors directed to the measurement of hydrogen, oxygen and glucose have been described in, inter alia, Kaplan, S. et. al.: Shunt Detection With Hydrogen, Ascorbate and Oxygen Electrodes. In: *Intravascular Catheterization*. (Eds) Zimmerman, H. A. and Thomas C. C., Springfield, Ill. (1977), U.S. Pat. Nos. 2,913,386 and 3,380,905, as well as in Clark, L. C. et. al.: Implanted Enzymatic Glucose Sensor. *Diabetes Care*. 5(3):174–180 (May-June, 1982), respectively. The hydrogen electrochemical sensors used in man for example can rely upon potentiometry for detecting dissolved hydrogen. To this end, such sensors measure a voltage or potential generated from the oxidation of hydrogen which is a function of the amount of hydrogen present. The oxygen and glucose electrochemical sensors on the other hand can rely upon polarography for detecting oxygen and glucose content. Polarography basically depends upon the measurement of a current at known applied voltages during the electrolysis of a solution between two or more electrodes. As to the polarographic measurement of oxygen, such a sensor is used as a cathode to detect a current generated from the reduction of oxygen by electrons which corresponds to the amount of oxygen. With respect to glucose, the sensor is generally employed as an anode to detect a current derived from the oxidation of hydrogen peroxide generated from reacting glucose with glucose oxidase in the presence of oxygen.

Unfortunately, the electrochemical sensors provided hitherto, including potentiometric and polarographic sensors, are virtually limited because of design specificity for measuring a particular chemical substrate such as hydrogen, oxygen, or glucose. Obviously, such a limitation can in some instances present undesirable drawbacks with respect to the inherent reliability of the information obtained from an electrochemical sensor notwithstanding the specific "intelligence" conferred thereto. For instance, all methods utilizing glucose oxidase to measure glucose requires the simultaneous presence of both oxygen and glucose in the material. In other words, the availability of oxygen for reaction with glucose, i.e., actual oxygen concentration in the body fluid or material, is a limiting factor for the glucose oxidation reaction. Yet, the art currently available has not heretofore accounted for such a limitation imposed by availability of oxygen on the sensors which depend on glucose oxidation for measuring glucose content in body fluids or other materials. Thus, the art is presently unable to insure that the current generated from the oxidation of glucose is in fact proportional to the glucose content in the body fluids or material being analyzed.

In one attempt to overcome the deficiency described above, U.S. Pat. No. 4,452,682 discloses an apparatus for electrochemically measuring items of blood relying upon a flow through system which comprises a blood pH/gas component sensor unit, an electrolyte component sensor unit, and/or a biochemical component sensor unit arranged in a series wherein a sampler and the sensor units are in communication with one another through a blood sample flow or channel. More particularly, the biochemical component sensor comprises an oxygen sensor electrode for detecting the dissolved oxygen concentration interconnected in a series to a glucose sensor electrode for measuring the glucose content.

In another attempt directed to the deficiencies aforementioned, U.S. Pat. No. 4,431,004 discloses a method and apparatus for more accurate measurements of glucose content in body fluids by sensing the absolute level of oxygen concentration in the fluid and correcting the output differential measurement indicative of the glucose content in the fluid according to the absolute level of oxygen. To accomplish the above, U.S. Pat. No. 4,431,004 employs an unaltered oxygen sensor interconnected to an altered oxygen sensor formed into a glucose sensor and positioned between the unaltered oxygen sensor and the body fluid to be analyzed for measuring the level of oxygen and glucose which constitutes a more accurate reading for the glucose content in the body fluid being analyzed.

Consequently, all of the electrochemical sensors provided hitherto invariably necessarily require a series or combination of sensors to measure a substrate and a chemical entity such as oxygen to assure a more accurate and reliable reading of a particular substrate being analyzed. Such a requirement for a series or combination of sensors contributes to the overall size of the electrochemical sensor adversely affecting the feasibility and undesirability of implantability of the sensors for in vivo detection. Thus, there are needs for electrochemical sensors having the capability of measuring with specificity a substrate and a chemical entity such as oxygen to help better determine the reliability of the substrate being detected.

SUMMARY OF THE INVENTION

In brief, the present invention seeks to alleviate the above-indicated problems and short-comings of the present state of the art and is directed to a new and improved polarographic method for measuring an anodically active product in animal tissue and oxygen in the enzymatic reaction layer of the sensor. The method comprises placing an electroenzymatic sensor having a sufficient amount of an enzyme selected for an analyte in contact with the animal tissue, subjecting the sensor to a suitable voltage for generating an anodic current, subjecting the sensor to a suitable voltage for generating a cathodic current, and detecting the anodic current as a measure for the analyte and the cathodic current as a measure for the oxygen in the enzymatic reaction layer of the sensor. More specifically, the method is conducted by contacting the analyte in the animal tissue with an enzyme selected for the analyte being analyzed, reacting the analyte with the enzyme, reducing the oxygen in the enzymatic reaction layer of the sensor, and directly detecting the conditions of the animal tissue as a measure of the amount of analyte and the amount of oxygen in the enzymatic reaction layer of the sensor. The procedure is virtually non-invasive or is non-invasive after one implant of the electroenzymatic sensor.

In a preferred embodiment, the electro-enzymatic sensors of this invention are implanted in, on, or near animal tissue and the enzyme is reacted with the analyte in or near the animal tissue. Conditions of the reactions such as the amount of consumed hydrogen peroxide and the reduction of oxygen are detected as a measure of the amount of analyte and oxygen present in the enzymatic reaction of the sensor, respectively. The types of animal tissues selected for implantation include both blood sites and non-blood sites.

In another embodiment, it is discovered that in vivo conditions around an implanted electro-enzymatic sensor site can be analyzed to determine if analyte measurement or functioning status of the sensor are reliable. For instance, a hydrogen or oxygen gas may be administered to an animal including a human by inhalation for generating an anodic or cathodic current, respectively. The duration of the detected currents derived from the hydrogen gas or oxygen gas can function as a measure of the blood flow around the sensor.

Thus, it can be appreciated that the special features and advantages of this invention make the methods highly unique and convenient for measuring anodically active analytes and oxygen in the enzymatic reaction layer of the sensors with an electroenzymatic sensor.

The above and other features and advantages of the invention, including various novel details of the methods, will now be more particularly described with reference to the accompanying figures and pointed out in the claims. It will be understood that the particular methods embodying the invention are exemplary only and not as a limitation of the invention. Any variation of the principals and features of the methods of this invention that do not depart from the scope of the invention are embraced herein.

DETAILED DESCRIPTION OF THE INVENTION

By way of illustrating and providing a
By way of ill better appreciation of the present invention, the following detailed description is given concerning the methods of the invention.

By the term "animal tissue" as used herein, it is meant to include all animal tissues including body fluids and blood. By the term "analyte", it refers to any material suitable for analysis with polarographic techniques. Exemplary of analytes that can be detected with the teachings of this invention include, for instance, glucose and lactate. With respect to the term "anodically active product", it is meant to refer to a product generated from the enzymatic reaction of the analyte and enzyme which can generate an anodic current when in contact with an electroenzymatic sensor subjected to a sufficient voltage.

In accordance with the present invention, it is directed to providing polarographic methods for measuring an anodically active product in animal tissue and oxygen at the enzymatic reaction layer of the sensor in vitro or in vivo. This is accomplished in the present instance by means of placing an electro-enzymatic sensor having a sufficient amount of an enzyme selected for the analyte being analyzed in contact with an animal tissue, subjecting the sensor to a sufficient voltage to generate a cathodic current, reversing, if desired, the polarity of the sensor, subjecting the sensor to a sufficient voltage to generate an anodic current and detecting the generated anodic current which functions as a measurement of the analyte and the generated cathodic current which functions as a measure of the oxygen in the enzymatic reaction layer of the sensor. The voltage applied may be fixed or switched between an anodic and cathodic voltage over time for generating anodic and cathodic currents, respectively. When the voltage is fixed, it may be applied in a range of about 0.5 to about 1.0 negative or positive volts for detecting the oxygen or analyte, respectively. Preferably, the fixed voltage should be at about −0.6 volts when detecting oxygen and +0.6 volts when detecting the analyte, such as glucose.

In accordance with a further aspect of this invention and as aforementioned, the methods may be conducted in vivo or in vitro. When conducting the methods in vitro, the measurements should preferably be made in, for example, a suitable amount of a magnetically stirred buffer or blood in, for instance, a glass chamber jacketed with water circulating at about 37° C. Exemplary of buffers suitable for use include phosphate buffers, such as Gomori buffer.

The electroenzymatic sensors to be used herein are well known in the art and generally are based upon the reaction of an analyte with oxygen as catalyzed by an enzyme selected for the analyte being measured. It should be understood, however, that the measurement of a selected analyte corresponds to the anodic current developed from the oxidation of hydrogen peroxide generated from the above described reaction, and not upon the measurement of $pO_2$. For instance, when glucose (analyte) is selected for analysis in accordance with the methods of this invention, glucose oxidase is reacted with the glucose in the presence of oxygen for generating hydrogen peroxide (anodically active product) and gluconic acid. The generated hydrogen peroxide diffuses to the anode where it is oxidized, i.e., removal of electrons to generate an anodic current which directly corresponds to the amount of glucose present in the animal tissue. In measuring oxygen with the same electroenzymatic sensors in accordance with the methods of this invention, the polarity of the sensor is reversed rendering the sensor a cathode. The oxygen available in the animal tissue diffuses to the cathode where it is reduced, i.e., the addition of electrons, to generate a cathodic current which corresponds to the amount of oxygen in the enzymatic reaction layer in the sensor. By the term "oxygen in the enzymatic reaction layer in the sensor", it refers to the oxygen that results from the kinetic equilibrium of the analyte and oxygen catalyzed by the enzyme.

In reversing the polarity in accordance with this invention, the sensor advantageously becomes capable of measuring "anodically active analytes" as well as oxygen. Thus, additional "intelligence" can be conferred upon electroenzymatic sensors utilizing the methods of this invention that has been heretofore unavailable. The value of the increased intelligence provides means for analyzing not only the environment surrounding the sensor for determining the reliability of the sensor as well as measurements of the analyte being analyzed, but also additional biological materials.

A typical electroenzymatic sensor that may be employed with the teachings of this invention consists preferably by forming a spherical bead on the end of a 10 cm length of 28 gauge platinum wire. The wire can then be inserted into a small base of silastic tubing and sealed with silastic cement and/or with many turns of fine thread. The thread sutures can be secured with cyanoacrylate cement or other suitable cements. The platinum beads can be used with an enzyme sandwiched between the platinum beads and a membrane. Completed enzyme electrodes can be used as made or preferably first treated with glutaraldehyde. Nevertheless, any suitable electroenzymatic sensor may be used. The report of Clark et al: Implanted Electroenzymatic Glucose Sensors. *Diabetes Care* 5 (3) 174–180 (May-June, 1982) and U.S. Patent Nos. 4,401,122 and 4,458,686 disclose in detail an electroenzymatic glucose sensor that may be employed with the teachings of this invention and are incorporated herein by reference in their entirety.

In a further aspect of this invention, it is directed to a method of detecting an in vivo condition around the sensor site comprising administering to an animal including a human by inhalation a sufficient amount of a gas wherein the gas dissolves in the animal tissue, detecting the current derived from the gas, and determining the duration of the current which functions as an indication of the in vivo condition around the sensor. The types of conditions that can be analyzed around the sensor site include, for example, oxygen tension and blood flow. Any type of gas suitable for inhalation, capable of permeating the membranes employed with the sensors, and generating a current may be utilized. Preferably, a hydrogen gas and oxygen and most preferably a blend of air and hydrogen gas or pure oxygen should be employed. Uniquely, hydrogen ions do not interfere with the anodic current generated from the oxidation of hydrogen peroxide making the use of hydrogen gas advantageously suitable for measuring blood flow around a sensor site, particularly when the analyte detected is glucose.

More specifically, to determine, for instance, the blood flow around the sensor, a mixture of air and hydrogen gas can be inhaled by an animal having an implanted electroenzymatic sensor. The duration of the anodic current derived from the hydrogen ion in the gas corresponds directly to the blood flow around, at or near the sensor site as determined by, for example, a hydrogen clearance curve. The measurement of hydrogen can be performed, for example, by the techniques discussed in Young, W.: H$_2$ Clearance Measurement of Blood Flow: A Review of Technique and Polarographic Principles. Stroke. 11(5):552–564 (Sept.-Oct., 1980), which is incorporated herein by reference. Likewise, if pure oxygen is inhaled by an animal, the duration of the generated cathodic current also corresponds to the blood flow. In other words, the response time to the generated currents can be used as a practical indication of good conditions for measuring analytes, such as glucose, since a supply of oxygen is necessary for the enzymatic reaction to produce the hydrogen peroxide used in the actual analyte measurements. Because of this critical limitation, it should be understood that the sensors with its membrane types and configurations should be made to be analyte diffusion limited and not oxygen diffusion limited. Further, when glucose is being measured, glucose oxidase derived from sources such as *Penicillin notatum* may have more favorable electroenzymatic oxygen/glucose kinetics.

In addition to measuring blood flow, the duration of a generated cathodic current derived from the administration of inhaled oxygen may also be utilized to reflect the oxygen tension surrounding the sensor site. Further, the inhalation of a gas by an animal under this method may also be utilized to determine the functional status of the sensor itself. For example, the response time is indicative of whether a sufficient amount of oxygen is present in the enzymatic reaction layer in the sensor or whether the sensor itself is functioning properly.

With respect to implantation of the electro-enzymatic sensors in an animal, any known technique not inconsistent with this invention may be employed. Exemplary of such a technique is described in Clark, L. C. et. al.: Theoretical and Practical Bases for Implantable Glucose Sensors with Special Reference to the Peritoneal, Proceedings of the Symposium on Biosensors, Los Angeles, Calif., Sept. 15/17, 1984, A. R. Potvin and M. R. Neuman (ed.), Instituted of Electrical and Electronics Engineers (IEEE), New York, N.Y., pp. 69/74 (1974) which is incorporated herein by reference in its entirety. As to the site of implantation, the sensors may be implanted in both blood and non-blood sites. Exemplary of non-blood sites include subcutaneous, intramuscular, epihepatic, intraperitoneal and brain sites, and most preferably intraperitoneal sites. With respect to the intraperitoneal sites, the sensor may be implanted in, on or near, but not limited to, the pancreas, liver, peritoneum, stomach, or intestines.

In a further feature contemplated by the present invention, the measurement of oxygen in an animal tissue at or around the sensor site can be determined once the glucose content of the tissue and the oxygen content in the sensor reaction layer has been measured. This can be accomplished by, for instance, formulating a table which relates the determined glucose content to the determined oxygen content in the sensor reaction layer. The value obtained from the glucose content and the oxygen content in the sensor reaction layer can be compared to known oxygen partial pressures determined by known techniques, such as an oxygen sensor, which functions as a measure of the oxygen in the tissue at or around the sensor site.

In a further aspect of the invention, a two electrode or three electrode system may be utilized. These systems are well known in the art. Generally speaking, the two electrode system is suitable for measuring substrates in aqueous solutions whereas three electrode systems are suitable for measuring substrates in solution with low conductivity.

The present invention may, of course, be carried out in other specific ways than those herein set forth without departing from the spirit and essential characteristics of the invention. The present embodiments are, therefore, to be considered in all respects as illustrative and not restrictive and any changes coming within the meaning and equivalency range of the appended claims are to be embraced therein.

What is claimed is:

1. A polarographic method for detecting both an analyte and oxygen with a detecting electrode of an electro-enzymatic sensor having at least two or more electrodes, said method comprises:

contacting the analyte with the detecting electrode wherein the detecting electrode includes an enzymatic reaction layer containing an enzyme for reacting with the analyte in the presence of oxygen to generate an anodically active product;

exposing the same detecting electrode having a first polarity to a voltage for generating an anodic current derived from the anodically active product generated from the reaction between the enzyme and the analyte in the presence of oxygen;

reversing the polarity of the same detecting electrode;

exposing the same detecting electrode having a polarity opposite said first polarity to a voltage for generating a cathodic current derived from electrochemically reducing the oxygen in the enzymatic reaction layer; and detecting both the anodic current and the cathodic current generated from the same detecting electrode as a function of the analyte and the oxygen, respectively, in the same enzymatic reaction layer.

2. A method of claim 1 further comprising implanting the electroenzymatic sensor in or on any tissue in an animal for in vivo measurement of the substrate and oxygen.

3. A method of claim 2 wherein the animal tissue is a non-blood site.

4. A method of claim 3 wherein the non-blood site is selected from the class consisting of a subcutaneous, intramuscular, epihepatic, intraperitoneal or brain site.

5. A method of claim 2 further comprising detecting an in vivo condition around the sensor site comprising administering to the animal by inhalation a gas wherein the gas dissolves in the animal tissue, detecting the current generated by the dissolved gas, and determining the duration of the current which functions as an indication of the in vivo condition around the sensor.

6. A method of claim 5 wherein the dissolved gas is selected from the class consisting of a hydrogen gas or an oxygen gas.

7. A method of claim 6 wherein an anodic current derived from the dissolved hydrogen gas is detected and a cathodic current derived from the dissolved oxygen gas is detected.

8. A method of claim 7 wherein the in vivo condition is blood flow.

9. A method of claim 1 wherein the analyte is selected from the class consisting of glucose or lactate.

10. A method of claim 9 wherein the enzyme is glucose oxidase when the analyte is glucose and lactate oxidase when the analyte is lactate.

11. In a polarographic method for detecting glucose and oxygen with an electroenzymatic sensor having at least two or more electrodes, the improvement comprises:

contacting the glucose with a detecting electrode of the electroenzymatic sensor wherein the detecting electrode includes an enzymatic reaction layer containing glucose oxidase for reacting with the glucose in the presence of oxygen to generate gluconic acid and hydrogen peroxide;

exposing the same detecting electrode having a first polarity to a voltage for generating an anodic current derived from the hydrogen peroxide produced from the reaction between the glucose and glucose oxidase in the presence of oxygen;

reversing the polarity of the same detecting electrode;

exposing the same detecting electrode having a polarity opposite said first polarity to a voltage for generating a cathodic current derived from electrochemically reducing the oxygen in he enzymatic reaction layer; and detecting the anodic current and the cathodic current generated from the same detecting electrode as a function of the glucose and the oxygen, respectively, in the same enzymatic reaction layer.

* * * * *